United States Patent
Yuds et al.

(10) Patent No.: US 11,179,508 B2
(45) Date of Patent: Nov. 23, 2021

(54) DIALYSIS MACHINE TUBING PROTECTION

(71) Applicant: Fresenius Medical Care Holdings, Inc., Waltham, MA (US)

(72) Inventors: David J. Yuds, Hudson, NH (US); Eric J. Bergman, Kalispell, MT (US); Maria T. Tamayo-Coffey, Pleasanton, CA (US); Jonathan F. Leclerc, Northborough, MA (US); Jessica M. Steuber, Ashland, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 309 days.

(21) Appl. No.: 16/391,576

(22) Filed: Apr. 23, 2019

(65) Prior Publication Data
US 2020/0338250 A1    Oct. 29, 2020

(51) Int. Cl.
*A61M 25/02*    (2006.01)
*A61M 1/28*     (2006.01)
*A61M 16/08*    (2006.01)

(52) U.S. Cl.
CPC ........... *A61M 1/285* (2013.01); *A61M 25/02* (2013.01); *A61M 16/0875* (2013.01);
(Continued)

(58) Field of Classification Search
CPC .......... A61M 1/285; A61M 2025/0206; A61M 2025/0233; A61M 2025/028;
(Continued)

(56) References Cited

U.S. PATENT DOCUMENTS

| | | | |
|---|---|---|---|
| 8,096,300 B2 * | 1/2012 | Russo | A61M 16/0488 128/207.17 |
| 2009/0149776 A1 * | 6/2009 | Adams | A61M 1/285 600/584 |

FOREIGN PATENT DOCUMENTS

| | | |
|---|---|---|
| CN | 204745132 | * 11/2015 |
| CN | 204745132 U | 11/2015 |
| JP | 2012040145 A | 3/2012 |

OTHER PUBLICATIONS

International Search Report and Written Opinion for International application No. PCT/US2020/027613, dated Nov. 4, 2020,17 pages.

* cited by examiner

*Primary Examiner* — Deanna K Hall
(74) *Attorney, Agent, or Firm* — Kacvinsky Daisak Bluni PLLC

(57) ABSTRACT

Tubing protectors, systems including tubing protection, and methods for protecting tubing, are disclosed, such as for protecting tubing connected between a patient and a dialysis machine (e.g., peritoneal dialysis machine) during a dialysis treatment. A tubing protector may include a tubing sheath attachable to a patient. The sheath may include a first portion for receiving and protecting a length of tubing extendible in the sheath, such as to minimize collapse, kinking, blockage, or combinations thereof, along the length of the tubing. A second portion may comprise a flexible material and enclose the first portion. The first portion may comprise a resilient material, which allows for movement in the sheath and has a strength to allow for reorientation of the tubing, while withstanding deformation of the tubing along the length. The first portion may be a coil, a plurality of rings, a woven mesh, or a solid tube, or combinations thereof.

19 Claims, 4 Drawing Sheets

(52) U.S. Cl.
CPC .............. *A61M 2025/0206* (2013.01); *A61M 2025/028* (2013.01); *A61M 2205/18* (2013.01); *A61M 2205/3306* (2013.01); *A61M 2205/3317* (2013.01); *A61M 2205/3334* (2013.01); *A61M 2205/3368* (2013.01); *A61M 2205/3553* (2013.01)

(58) Field of Classification Search
CPC .......... A61M 2205/18; A61M 2205/33; A61M 2205/3306; A61M 2205/3317; A61M 2205/3334; A61M 2205/3368; A61M 2205/35; A61M 2209/088; A61M 25/02
See application file for complete search history.

DIALYSIS MACHINE TUBING PROTECTION

FIELD

The disclosure generally relates to tubing protectors, systems including tubing protection, and methods for protecting tubing, for example, as used with dialysis machines and systems, and more particularly to tubing protection for tubing extending between a patient and a peritoneal dialysis machine while performing a dialysis treatment.

BACKGROUND

Dialysis machines are known for use in the treatment of renal disease and for utilizing tubing connected between the machines and patients during treatments, which may require protection to prevent or minimize collapse, kinking and/or blockage, along a length of the tubing. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A dialysis machine, such as a peritoneal dialysis machine, may include one or more containers (e.g., bags) containing a fluid, e.g., a dialysate, for patient infusion. In peritoneal dialysis machines, for example, tubing as one or more fluid lines are inserted into an abdomen of a patient for flowing fresh dialysate and removing used dialysate, waste, contaminants, and excess fluid. Treatments may require several batches of fresh and used dialysate to cycle in and out of the patient's abdomen over a several hour period, often overnight. The PD cyclers may therefore perform a dialysis treatment substantially automated and unsupervised while the patient sleeps. With such treatments, for example, circumstances of the location, posture, or movement, of patients may compromise the tubing connected to them, resulting in instances of collapse, pinching or kinking, and/or blockage, of the tubing, particularly at points close to where the tubing connects to the patients.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In some embodiments of the present disclosure, a tubing protector may comprise a tubing sheath. The sheath may include a first portion. The first portion may be for receiving and protecting a length of tubing extendable therein, so as to minimize collapsing, kinking, or blockage, or combinations thereof, along the length of the tubing. The sheath may include a second portion enclosing the first portion, and the second portion may comprise a flexible material. The first portion may comprise a resilient material, and the resilient material may allow for movement in the sheath and may have a strength to allow for reorientation of the tubing, while withstanding deformation of the length of the tubing.

In the embodiments described and other embodiments of the present disclosure, the tubing may further comprise a belt connected to the tubing sheath and removably attachable to a patient. The first portion may be a coil, a plurality of rings, a woven mesh, or a solid tube, or combinations thereof, such that the first portion may be extendable along the length of the tubing. The second portion may be a cover over the first portion and may be extendable along the length of the tubing. The second portion may include a slot extending along the cover and the length of the tubing. The tubing may be connectable between a patient and a peritoneal dialysis machine, and the tubing sheath may be attachable to the patient with the belt for a dialysis treatment. A tubing protector may further comprise one or more sensors configured to detect a fluid temperature, a fluid flow rate, a fluid pressure, a kink, collapse or blockage of the tubing, or patient parameters, or combinations thereof. The tubing sheath, or the belt, or both, may further comprise a connectivity component for data transmission between one or more sensors and the peritoneal dialysis machine.

In some embodiments of the present disclosure, a tubing protection system may comprise a tubing sheath surrounding a length of tubing extendable therein when connected to a patient. The sheath may be for minimizing collapsing, kinking, or blockage, or combinations thereof, along the length of the tubing. The tubing sheath may comprise a resilient material, and the resilient material may allow for movement in the sheath and may have a strength to allow for reorientation of the tubing, while withstanding deformation of the length of the tubing.

In the embodiments described and other embodiments of the present disclosure, the tubing sheath may include a coil, a plurality of rings, a woven mesh, or a solid tube, or combinations thereof. The tubing sheath may include a cover. A tubing protection system may further comprise a belt coupled to at least a portion of the tubing sheath. The belt may be removably attachable to the patient such that the tubing sheath may be positionable about the length of the tubing when attached to the patient. A tubing protection system may further comprise one or more sensors disposed on the tubing sheath, the cover, or the belt, or combinations thereof. The sensors may be configured to detect a fluid temperature, a fluid flow rate, a fluid pressure, a kink, collapse or blockage of the tubing, or patient parameters, or combinations thereof. The cover may include a slot extending along the length of the tubing. A tubing protection system may further comprise a connectivity component for data transmission to a remote device.

In some embodiments of the present disclosure, a method of protecting tubing connecting a patient to a peritoneal dialysis machine during a treatment may comprise receiving a length of the tubing closest to the patient in a tubing sheath. The sheath may be configured to minimize collapsing, kinking, or blockage, or combinations thereof, along the length of the tubing. The method may include connecting the tubing to the patient for performing the treatment with the peritoneal dialysis machine. The method may include attaching a belt around the patient to secure the tubing sheath and the length of the tubing received in the tubing sheath. The belt may be coupled to the tubing sheath, such that a substantially uninterrupted fluid flow may be provided through the length of the tubing between the peritoneal dialysis machine and the patient during the treatment.

In the embodiments described and other embodiments of the present disclosure, a method may further comprise detecting at least one of fluid temperature, a fluid flow rate, a fluid pressure, a kink, collapse or blockage of the tubing, or patient parameters, or combinations thereof, during the treatment. The tubing sheath may include a first portion. The first portion may comprise a resilient material and may have a strength to prevent deformation of the length of the tubing. The tubing sheath may include a second portion. The second portion may be formed of a flexible material and may enclose the first portion. The first portion may be a coil, a plurality of rings, a woven mesh, or a solid tube, or combinations thereof. The first portion may be extendable along the length of the tubing. The second portion may comprise a cover. The cover may include a slot extending along the length of the tubing.

BRIEF DESCRIPTION OF THE DRAWINGS

By way of example, specific embodiments of the disclosed machine will now be described, with reference to the accompanying drawings, in which.

DETAILED DESCRIPTION

Figure 1:
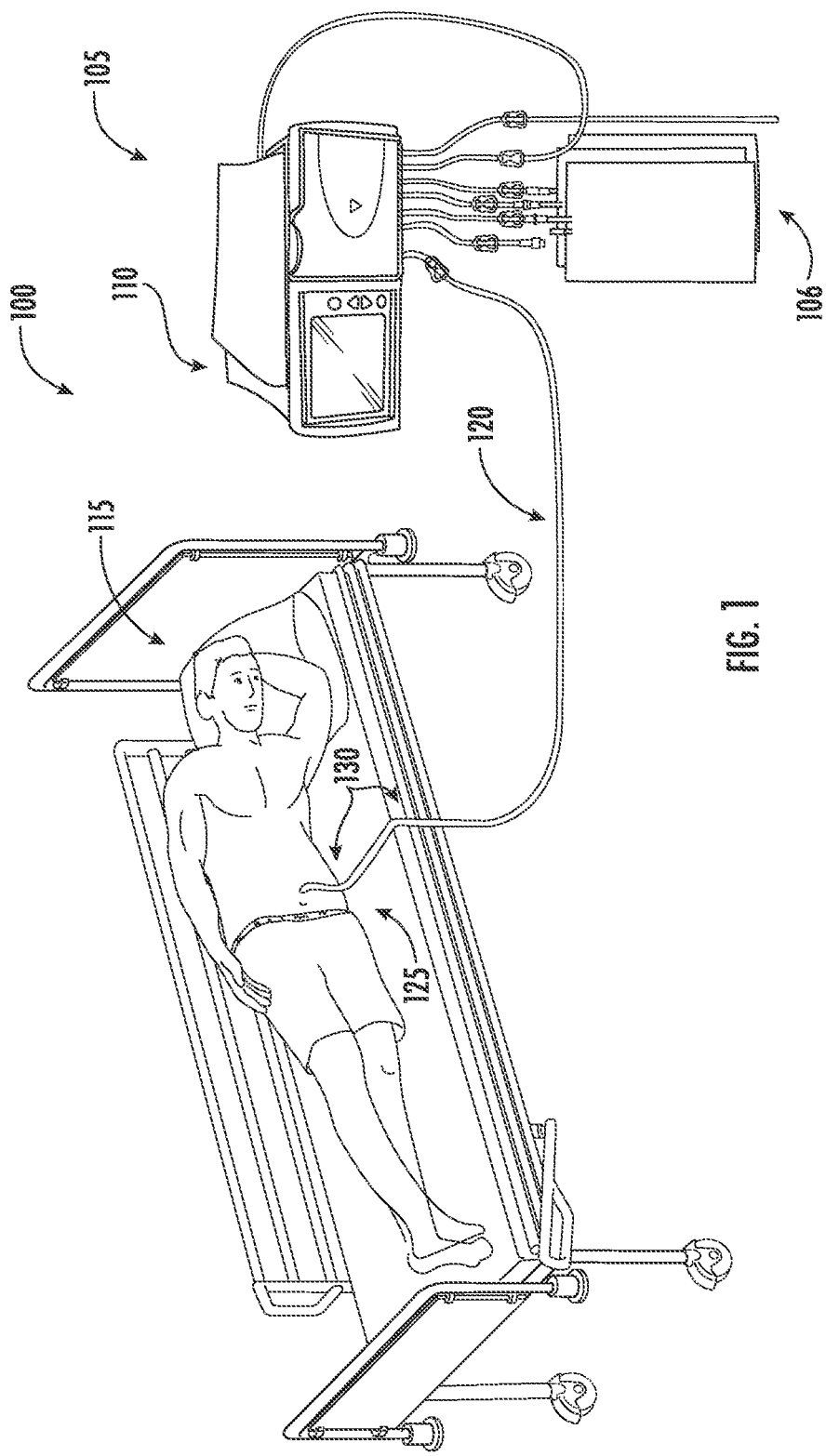
FIG. 1 illustrates a schematic of a peritoneal dialysis system connected to a patient to perform a dialysis treatment.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

As described above, in peritoneal dialysis operations, tubing is connected between a dialysis machine and a catheter in an abdomen of a patient for delivering fresh dialysate into the patient's peritoneal cavity and removing used dialysate and contaminants after a predetermined time. A patient may undergo several cycles of delivering a fresh batch of dialysate and removing the used dialysate and contaminants in a single treatment. In some embodiments, a peritoneal dialysis treatment may be performed at home, controlled by an automated peritoneal dialysis machine or cycler, and may occur overnight while a patient is sleeping, e.g., automated peritoneal dialysis (APD). In other embodiments, a peritoneal dialysis treatment may be performed manually, e.g., continuous ambulatory peritoneal dialysis (CAPD) procedures.

FIG. 1 is a schematic 100 illustrating a patient undergoing an overnight treatment by a peritoneal dialysis system 105. A dialysis machine, or PD cycler 110, may monitor the fluid flow to and from a patient 115. The patient 115, as illustrated, may be sleeping in a substantially horizontal position. It is also understood that the patient 115 may be sitting up and awake during treatment. Tubing 120, e.g., a patient fluid line, of the dialysis system 105 may extend between the PD cycler 110 and a catheter 125 extending from an abdomen (e.g., peritoneal cavity) of the patient 115. One or more dialysate bags 106 may be connected to the PD cycler 110, for providing fresh dialysate to the patient. The patient fluid line and the dialysate bags may be connected to each other and additional tubing via a cassette or cartridge. In embodiments, a patient line may be connected to the cartridge. The patient line may be connectable to the patient's abdomen (e.g., peritoneal cavity) via the catheter and the dialysis machine may be used to pass dialysate back and forth between the cartridge and the patient's peritoneal cavity during use with pump heads situated on the machine.

Positioning of the tubing 120 during a treatment may be subject to how and where the patient may be sleeping and/or sitting. The tubing 120 may become kinked, or may collapse, or become otherwise blocked anywhere along the length of the tubing between the patient 115 and the PD cycler 110. Specifically, tubing 120 may kink, collapse, and/or block near the patient 115, e.g., at the catheter 125, and/or where the tubing extends beyond a patient's sleeping area, e.g., off an edge of a bed, or chair, indicated at reference numeral 130. The patient 115 may inadvertently kink, collapse, and/or otherwise block the tubing during normal shifting and/or movement while asleep.

In response to detecting a potential kink, collapse, and/or blockage of the tubing 120, the PD cycler 110 may automatically alert, alarm, and/or abort a treatment if fluid cannot freely flow between the patient 115 and the PD cycler 110. The PD cycler 110 may detect the kinked or collapsed tubing to provide warnings to the patient prior to stopping treatment, which may wake the patient so that the tubing can be checked and readjusted as needed to continue the treatment. However, these warnings in the form of alerts and alarms may result in a patient having a restless evening, negating the advantages of performing the dialysis treatment overnight.

Figure 2A:
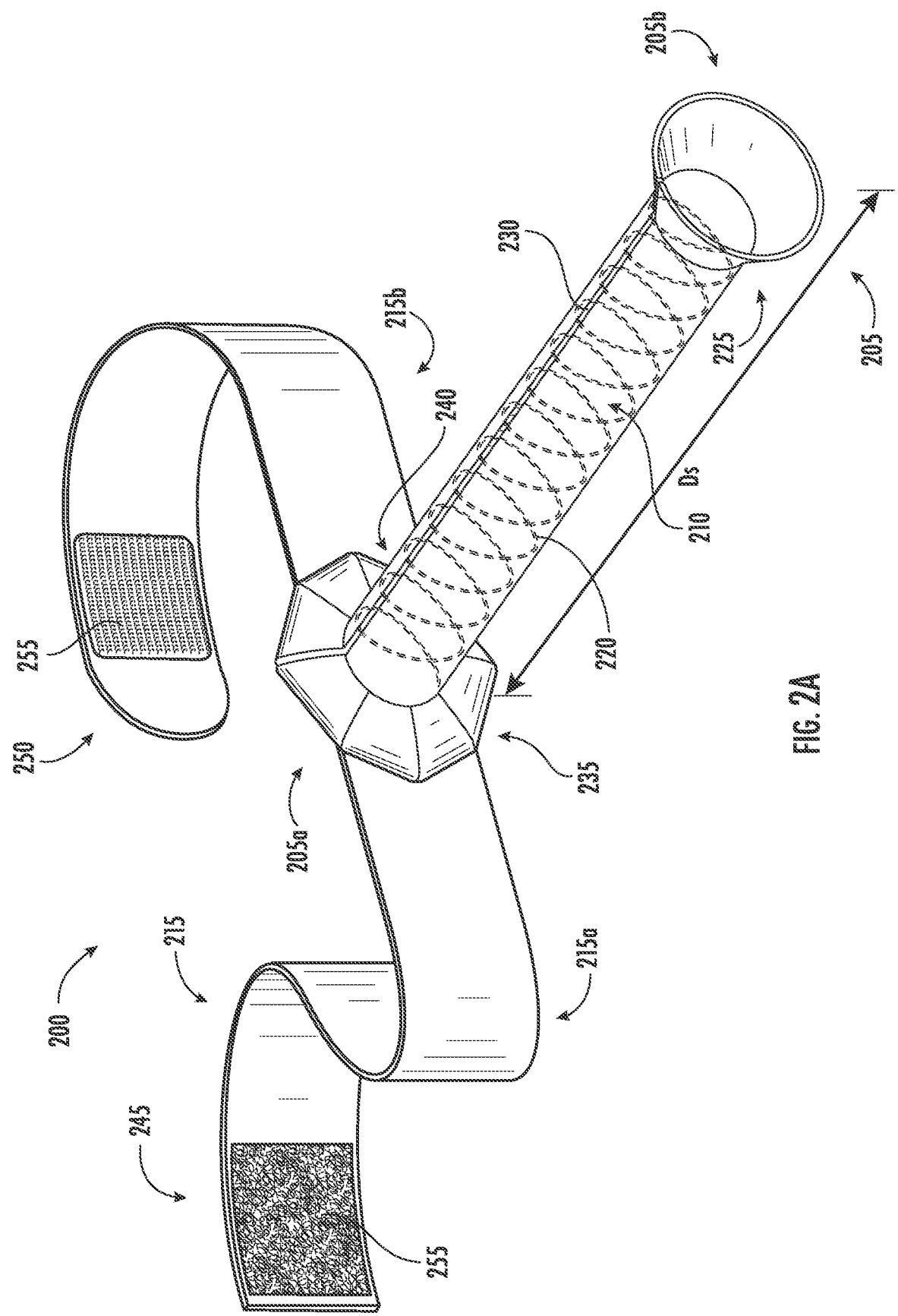
FIGS. 2A-2B illustrate an exemplary embodiment of a tubing protection system in accordance with the present disclosure.
Figure 2B:
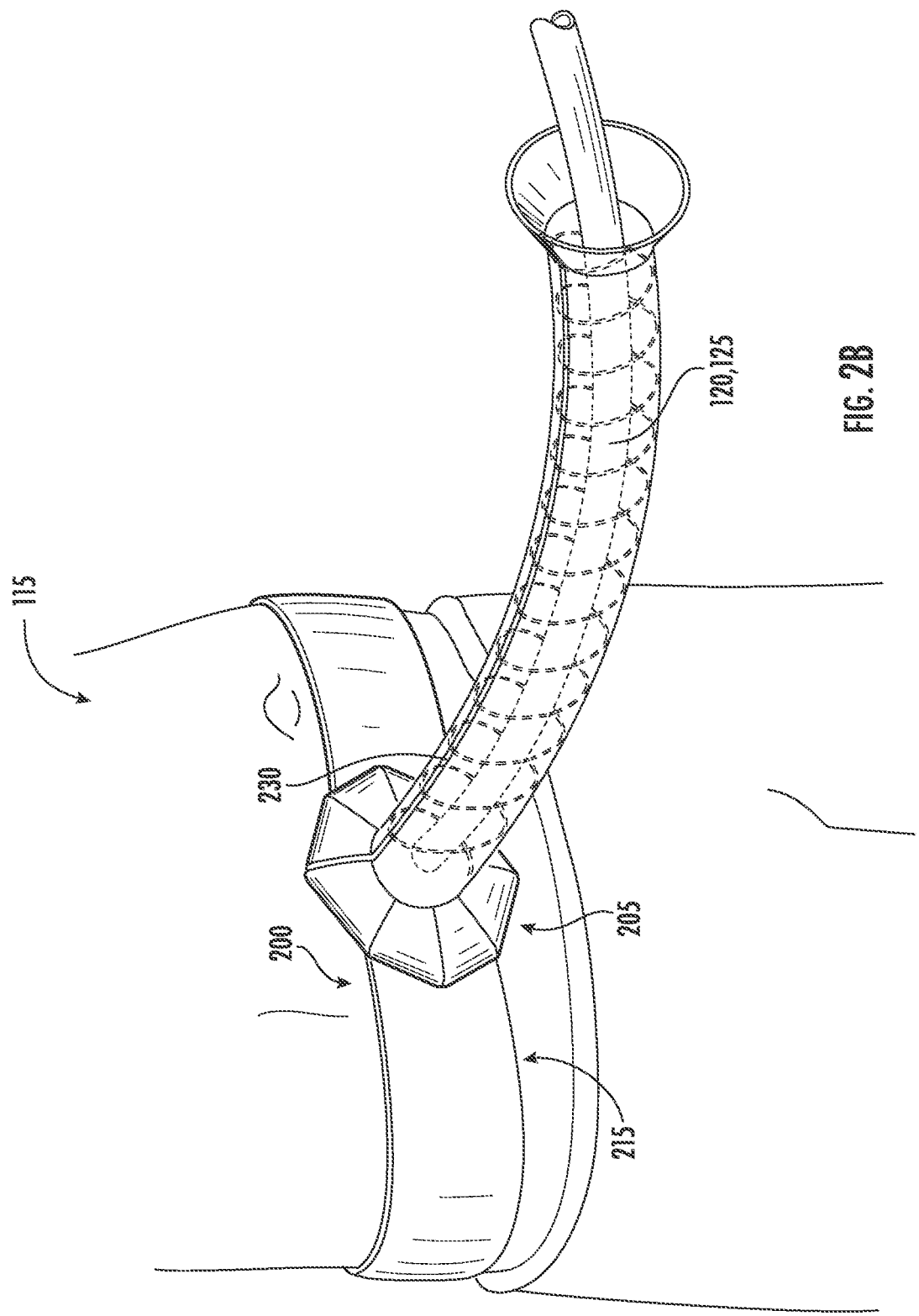
Figure 3:
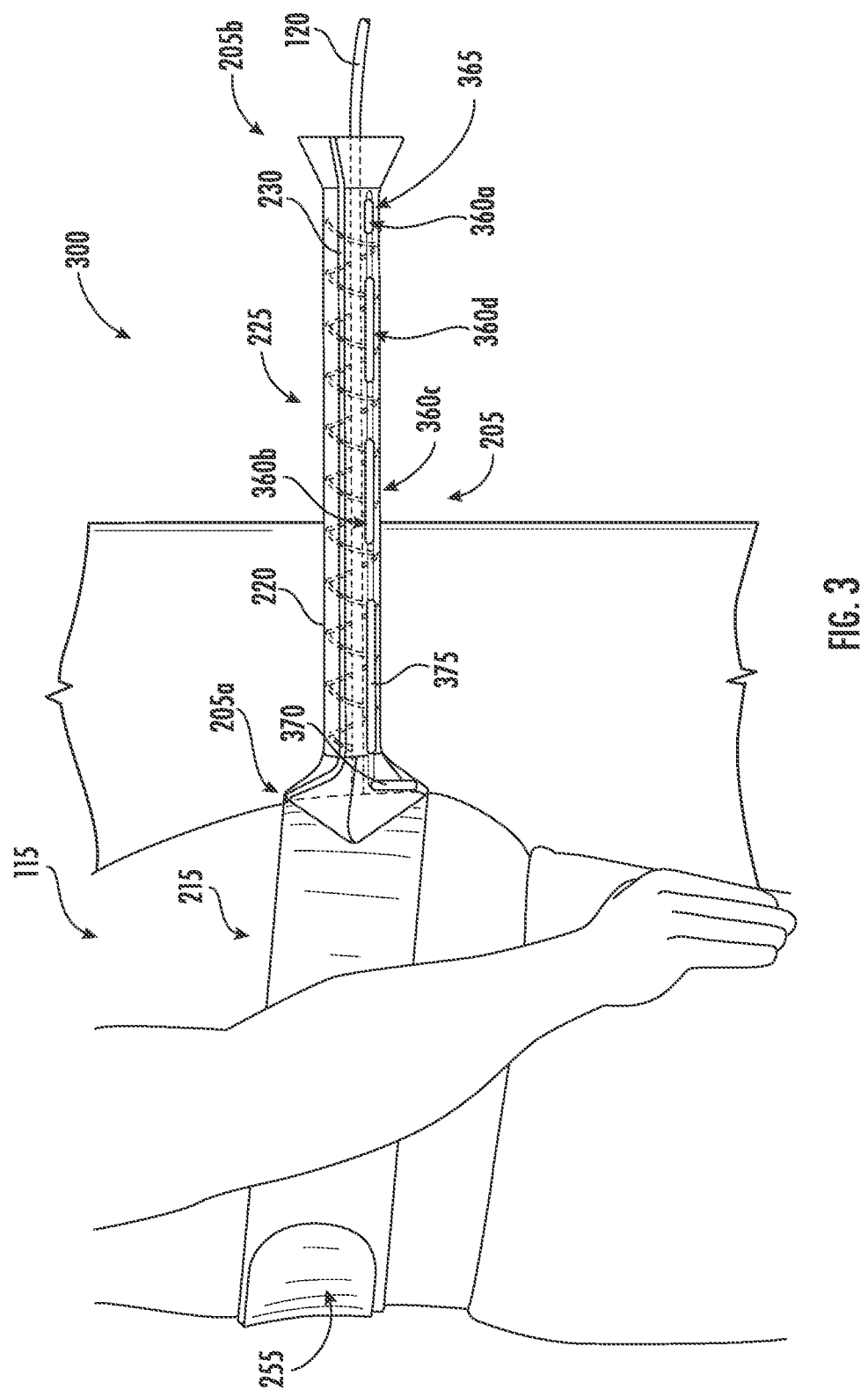
FIG. 3 illustrates a schematic of an exemplary embodiment of a tubing protection system in accordance with the present disclosure.

Referring now to FIGS. 2A-2B, and 3, exemplary embodiments of a tubing protector 200, 300 of the present disclosure are described, which may be utilized by a patient to minimize kinking, collapse, or blocking, or combinations thereof, during a treatment, such as a dialysis treatment with a peritoneal dialysis machine.

As shown in FIGS. 2A-2B, the tubing protector 200 may be attachable to a patient around a patient line or tubing, e.g., tubing 120. The tubing protector 200 may include a tubing sheath 205. The sheath 205 may include a proximal end 205a and a distal end 205b and may be extendable a distance "Ds". The distance Ds of the sheath 205 may be up to a length of the tubing 120, which may include an entire length of the tubing, e.g., so that the patient line may be completely enclosed by the tubing protector 200. In some embodiments, the distance Ds of the sheath 205 may be less than an entire length of the tubing 120. The sheath 205 may be formed as a tube, e.g., having a hollow body to define a cavity 210, so that the tubing 120 may be extendable through the cavity 210 from the patient at the proximal end 205a of the sheath 205 and through the distal end 205b of the sheath 205 to the PD cycler 110. The sheath 205 may be substantially cylindrical, although it is envisioned that the sheath 205 may be any shape to enclose the tubing 120.

In some embodiments, the proximal end 205a of the sheath 205 may be a larger diameter than a diameter of the distal end 205b. The proximal end 205a of the sheath 205 may transition from a larger diameter to a smaller diameter, e.g., may be formed as a frustoconical portion. The frustoconical portion may extend a distance along the sheath away from the patient to accommodate the length of the catheter 125 extending from the abdomen (e.g., peritoneal cavity) of the patient 115, although in other embodiments may be any distance to receive the tubing 120 and the catheter 125. It may be advantageous to have a larger proximal end 205a to accommodate any additional space needed around the catheter 125 extending out of the patient's abdomen. For example, the catheter 125 and/or the skin immediately surrounding the area of insertion may be sensitive and/or susceptible to infection. The larger proximal end 205b may minimize patient discomfort and/or infections by covering over the catheter 125 and tubing 120, and the area of insertion, and tapering to a smaller diameter away from the catheter 125. Additionally, and/or alternatively, the larger proximal end 205a may be sized to accommodate a belt 215.

In some embodiments, the sheath 205 may include a first portion 220 and a second portion 225. The first portion 220 may be formed to protect the tubing 120 to minimize or prevent kinking, collapse, or blockage, or combinations thereof, along the length of the tubing. In some embodiments, the first portion 220 may comprise a resilient material; the material being strong enough so that when the tubing 120 is received in the cavity 210, the tubing 120 may be sufficiently supported when a patient readjusts and/or moves while sleeping during a treatment, so that fluid flow (e.g., fresh dialysate, used dialysate, waste, contaminants, excess fluid, etc.) is uninterrupted or substantially uninterrupted. An uninterrupted or substantially uninterrupted fluid flow may minimize or eliminate alerts and/or alarms, so that the patient may not be woken up to attend to the alert and/or alarm. The resilient material of the first portion 220 may be of a material and configured within the sheath to accommodate movements of the patient, and consequential reorienting of the tubing, while still reinforcing the sheath to protect and/or minimize the tubing against deformation, such as blocking, kinking and/or collapse.

The tubing 120 may be connected to the catheter 125 and extend from the patient in any orientation, e.g., substantially perpendicular, or following along the abdomen of the patient in any direction. For example, sheath 205 is depicted in FIGS. 2A-2B as being substantially straight, but may have one or more bends or twists, or the like, along the distance Ds, to orient the tubing as desired for comfort and accessibility, while still providing protection for the length of the tubing extending along and within the sheath. In embodiments following along the abdomen, the sheath may have a bend in close proximity to the connection of the tubing to the patient in order to orient the sheath in a configuration that is more parallel (i.e., presents a lower profile) to the torso of the patient. In some embodiments, the tubing 120 may be affixed to a stationary point a distance from the patient, e.g., a patient's bed or chair, to encourage a desired orientation of the tubing 120. Throughout the treatment, the tubing 120 may reorient itself as the patient moves while asleep, and the first portion 220 may be resilient and strong enough to accommodate this reorientation based on patient movement, but may not direct the orientation of the tubing. For example, if the patient moves so that the tubing is situated underneath a body part, the first portion 220 may be resilient enough to allow for this patient movement, and may also be strong enough so as to not deform (e.g., kink, collapse, and/or block) under the patient's weight.

In embodiments, the first portion 220 may be formed of a coil, or a spring. The coil may extend from the proximal end 205a to the distal end 205b of the sheath 205, and may define the cavity 210. The coil may extend all the way to the proximal end 205a to a surface of the proximal end 205 that is in proximity to or in contact with the patient abdomen and around the catheter 125. The coil may reinforce, or further reinforce, the proximal end 205 in this regard. Alternatively, the coil may terminate in the sheath prior to reaching proximal end 205 and the first portion 220 may be continued from the termination of the coil to the proximal end 205 with a section of fabric, or other material, that is softer than the coil reinforced segment of the first portion, e.g., to provide a comfortable interface with the patient. If the coil extends to the proximal end 205, the diameter of the coil at the proximal end 205 may be made larger, or made to gradually become larger, compared to the diameter along other segments of the first portion 220. This may be done to accommodate a possible larger diameter of the catheter 125 at the proximal end 205 than, e.g., tubing 120 at other segments of the first portion. Alternatively, the coil diameter may be sized the same along all, or substantially all, of the length of the first portion in order to provide clearance for the largest diameter portion of the catheter and tubing along the first portion. In some embodiments, the first portion 220 may be a plurality of rings, extending from the proximal end 205a to the distal end 205b of the sheath 205, to define the cavity 210. A coil or a plurality of rings as the first portion may be made resilient by the material used (e.g., a memory material, such as nitinol) and how the material is configured (e.g., width and pitch of coil or rings) in the first portion of the sheath. The coil or rings may be configured for expanding and/or contracting from each other, in a direction along a longitudinal axis of the sheath and substantially parallel to the tubing 120.

In some embodiments, the first portion may be a woven mesh, or a solid tube, or both, which is resilient. The resiliency of the mesh or solid tube, e.g., the degree of flexibility/rigidity of the mesh or tube across a range of values and measures, may be varied according to the requirements of the specific application of the tubing protector, as may be understood in the art, e.g., by varying the material, the weave, the pitch of coil, etc. The first portion 220 may be formed of metals, metal alloys, composites, or any material that maintains its shape, or combinations thereof. The woven mesh as the first portion may be a plurality of woven wires forming a pattern. The wires and formed pattern may allow for elastic bending or other movement, which may allow the sheath 205 to respond to patient movement during a treatment. Other reinforcing options are contemplated, as an alternative or complement to a mesh or coil. For example, in some embodiments, the first portion may be a linear hollow cylinder (e.g., balloon), which is inflatable along its length. The cylinder may be uniform along the length, or may include inflatable and non-inflatable chambers, so as to allow for areas of varying flexibility/rigidity.

In some embodiments, the second portion 225 may be formed as a cover to enclose the first portion 220. The second portion 225 may be separate from the first portion 220, although it is also envisioned that the first and second portions 220, 225 may be integrally formed. For example, the first portion 220 may be embedded in the second portion 225. It is understood that the second portion 225 (e.g., cover) may enclose the first portion by extending over the first portion 220, by integrally including the first portion 220, or both.

The second portion 225 may comprise a flexible material, such as a soft material, a fabric, or any washable material. It may be advantageous to use a soft material for the second portion 225, particularly at the proximal end 205a of the sheath 205, which may directly contact the patient. A cover as the second portion 225 may be padded, e.g., may be softer, in some portions, such as the proximal end 205a, so that contact with the patient may not disrupt a sleep cycle of the patient or irritate the skin the of the patient. For example, padding may be included so that the tubing protector 200 may be more "huggable" along the patient's abdomen.

Additionally, a machine-washable material may allow for the tubing sheath 205 to be cleaned between uses so that the tubing protector 200 may be reusable and minimize potential infections through reuse. In other embodiments, the tubing protector 200, or portions of the tubing protector 200, may be single-use, and disposable after each treatment.

In some embodiments, the sheath 205 may include a slot 230, extending the distance Ds from the proximal end 205a to the distal end 205b of the sheath 205 and along a length of the tubing. The slot 230 may be an opening of the sheath 205, e.g., an opening in a cover extending along the longitudinal axis of the sheath, so that the catheter 125 and the tubing 120 may be quickly and easily inserted in the cavity 210 of the sheath 205 without having to thread the sheath 205 along the entire tubing 120 for positioning in proximity to the patient. It is understood that the slot 230 may be optional, and that in some embodiments, the tubing protector 200 may slide over the tubing 120 for positioning in proximity to the patient. The slot 230 may optionally be closable by sealing mechanisms, such as clips, buttons, snaps, Velcro®, or combinations thereof, for repeatable opening and closing of the slot 230. The slot 230 may also optionally be overlapping edges of the second portion, so that the tubing 120 may be slid between the edges into the cavity 210. It may be advantageous to be able to close the slot 230 so that the tubing 230 may be retained in the cavity 210 of the sheath 205.

The sheath 205 may be coupled to a belt 215, to removably attach the tubing protector 200 to a patient for use during a treatment. The belt 215 may extend from the proximal end 205a of the sheath 205. In some embodiments, a first side 215a of the belt 215 may extend from a first side 235 of the proximal end 205a of the sheath 205 to an end 245. A second side 215b of the belt 215 may extend from a second side 240 of the proximal end 205b of the sheath 205 to an end 250. In other embodiments, the belt 215 may extend from one side 235, 240, and attach directly to the other side 235, 240 of the proximal end 205b of the sheath 205. The belt 215 may hold the sheath 205 of the tubing protector 200 in place in proximity to the patient's abdomen, so that fluid flow in the tubing 120 may be uninterrupted or substantially uninterrupted. The belt 215 may be wide enough to comfortably extend around the patient's abdomen and lower back without shifting while a patient is asleep. In embodiments, the belt 215 may be formed of a washable, soft, flexible material, and/or may be at least partially elastic, to comfortably accommodate various sizes and positioning of patients.

The first and second ends 250 may include attachment mechanisms 255. The belt 215 may extend around the patient and secure to the patient by the attachment mechanisms 255. The attachment mechanisms 255 may be any securement mechanism, including but not limited to Velcro® fasteners, snaps, buttons, ties, hook and eyes, and the like. The attachment mechanisms 255 may be selected for patient comfort, e.g., so that the patient may comfortably wear the tubing protector 200 while sleeping and/or sitting, for long periods of time. Additionally, the attachment mechanisms 255 may be spaced apart to accommodate different-sized patients, to secure the tubing protector against the patient's abdomen.

Referring now to FIG. 3, another exemplary embodiment of a tubing protector 300 in accordance with the present disclosure is shown. Similar to the tubing protector 200, a sheath 205 having a proximal end 205a and a distal end 205b may be coupled to a belt 215, so that the tubing protector 300 may be removably attachable to a patient 115. Tubing 120 may extend through the cavity 210 of the sheath 205 and out the distal end 205b for connection into a treatment system, such as a PD cycler (e.g., via a cassette, cartridge, and/or warmer pouch).

Optionally, the tubing protector 300 may further include one or more sensors 360, and may be any of a temperature sensor, a fluid pressure sensor, a flow rate sensor, a conductivity sensor, a tubing kink and/or collapse sensor, a blockage sensor, a weight sensor, a video sensor, an air sensor, an air bubble sensor, a thermal imaging sensor, an electroencephalogram sensor, a motion sensor, an audio sensor, an accelerometer, or a capacitance sensor, or any combinations thereof. The sensors may be configured to detect fluid parameters, patient parameters, or both. It is appreciated that the sensors 360 may include sensors with varying sampling rates, including wireless sensors. Sensors 360 may include any type and/or design in the sheath 205, and the sheath 205 may include any number "n" of sensors, e.g., 360a, 360b, . . . 360n. Enhanced monitoring of patient parameters and/or fluid flow parameters may provide notification to the patient and/or a medical professional of the progress, efficacy, and/or efficiency of the treatment performed. In some embodiments, sensors 360 may be disposed in the cavity 210 of the sheath 205 and/or may be disposed anywhere along the distance Ds from the proximal end 205a to the distal end 205b in proximity of the tubing 120. The sensors 360 may be disposed on the first portion 220 and/or the second portion 225 of the sheath 205. Sensors 360 may additionally and/or alternatively be disposed on the belt 215.

The sheath 205 may include an optical sensor 360a for visual detection of a fluid. In some embodiments, a light emission source 365 (e.g., light emitting diode (LED)), may be disposed with the optical sensor 360a. The light emission source 365 may illuminate the fluid flowing through the tubing 120 for the optical sensor 360a to observe fluid flowing through the tubing 120, the rate of flow through the tubing, and/or to detect any changes in clarity of the fluid. For example, patients with an infection may have used dialysate fluid of a different (e.g., cloudier) clarity and/or particles in the fluid than patients without an infection, which may indicate peritonitis in the patient. More than one optical sensor 360a and/or light emission source 365 may be placed along the length of the sheath 205 to detect various of the above or other conditions. The optical sensor 360a and light emission source 365 may provide a more reliable and/or repeatable option for detecting changes in fluid. In some embodiments, the light emission source 365 may include a photodetector and circuitry such that upon detection of a change in clarity of fluid, the optical sensor 360a may signal to the patient or medical provider, or both.

The sheath 205 may include a flow rate sensor 360b for detecting a rate of flow in the fluid (e.g., fresh dialysate, used dialysate, waste, contaminants, excess fluid, etc.) flowing between the patient and the treatment system (e.g., PD cycler). The flow sensor 360b may detect an obstruction, or blockage, which may change the rate of flow of the fluid through the tubing 120. The flow rate sensor 360b may, e.g., detect when a fluid flow rate changes a predetermined amount, at a single point or over a predetermined sampling interval, in which case a signal may be issued to indicate a potential blockage to the patient.

A temperature sensor 360c may be disposed in or on the sheath 205, which may monitor a temperature of fresh dialysate prior to flowing into the patient. Although dialysate temperature may be regulated and monitored at the PD cycler, detecting the dialysate temperature closer to entering the patient may be advantageous for temperature regulation for patient comfort and safety, and/or as a redundant check on the temperature regulation at the PD cycler.

A conductivity sensor 360d may be disposed in the sheath 205 to detect and/or measure a conductivity of the fluid flowing between the patient and the PD cycler, including but not limited to fresh dialysate, used dialysate, waste, contaminants, excess fluids, etc. Conductivity levels may indicate if a fluid is acceptable. For example, fresh dialysate may be monitored to ensure it is within an acceptable predetermined conductivity range prior to being delivered to the patient, to ensure it has not been contaminated or otherwise become unsuitable for patient use. Conductivity levels of used dialysate, waste, contaminants, or other excess fluids flowing out the patient may be monitored for detecting patient health. The conductivity sensor 360d may detect a change in conductivity of fluid flowing out the patient, at a single point or over a timed interval, which may indicate a potential infection, illness, or other patient parameter. A signal may be issued to indicate to the patient and/or medical professional for further evaluation.

The sensors 360a, 360b, . . . 360n may signal to the patient or medical provider in the form of a notification, warning, alert, and/or alarm. In some embodiments, the notification may be at the treatment system, such as the PD cycler, e.g., on a display, in a warning light, a print out, or any other visual, audible, and/or haptic signal. In some embodiments, the notification may be at the sheath 205, e.g., as a visual, audible, and/or haptic signal. For example, a flow rate sensor 360b may be advantageous for manual peritoneal dialysis treatments, e.g., to provide feedback to a patient receiving treatment without a cycler by signaling to the patient via the tubing protector 200, 300. A temperature sensor 360c may be similarly advantageous for manual peritoneal dialysis treatments, e.g., to provide feedback to a patient not otherwise available. The patient may adjust a treatment to achieve a desired temperature including adjusting storage of dialysate bags and/or changing the location of the dialysis treatment.

In embodiments, dialysate may be stored in containers, e.g., a flexible bag, that may be formed of a Biofine™ material and/or a polyvinyl chloride (PVC) material. Although the term "bag" is used throughout, it should be understood that a dialysate bag may be any type of container capable of holding a fluid, e.g., a dialysate. In some embodiments, a fluid container may include a container in which dry concentrates are mixed with water to generate dialysate suitable for a dialysis treatment.

In some embodiments, the sheath 205 may include a haptic communication component 370, which may apply a force, vibration, or motion, or combinations thereof, to a patient, in response to a sensor 360a, 360b, . . . 360n detecting a condition that may necessitate immediately notifying the patient. For example, a sensor 360 may detect kinking or collapse of the tubing, or a risk of kinking or collapse. The haptic communication component 370 may be disposed at the proximal end 205a of sheath 205, so that the patient may feel a movement (e.g., force, vibration, or motion) of the haptic communication 370. Haptic signals may allow the patient to readjust position, e.g., sleep position, with respect to the tubing 120, and/or to readjust the position of the tubing 120 or the tubing sheath 205, in order to minimize, resolve and/or avoid an audible alarm from the PD cycler. The ability of the patient to self-correct may advantageously improve a patient's sleep cycle during overnight treatments, as well as the sleep cycle of other persons in a vicinity of a patient receiving an overnight treatment. Alternatively, and/or additionally, haptic signals may be more reliable for alerting patients with hearing loss.

In some embodiments, the sheath 205 or belt 215, or both, may include a connectivity component 375 for transmission of sensor data from the tubing protector 200, 300 to one or more remote devices, including but not limited to a PD cycler, other dialysis machine or system, healthcare databases, mobile devices, and the like. The connectivity component 375 may be Bluetooth® enabled, and may include any circuitry, microprocessor, microcomputer, or other components for transmitting sensor signals and/or notifications, warnings, alerts, or alarms, or combinations thereof, between the tubing protector 200, 300 and remote device.

While the systems and techniques described herein have been largely explained with reference to a dialysis machine, in particular, a peritoneal dialysis machine, a tubing protector may be used in connection with other types of medical treatment systems and/or machines, including any other medical treatment devices involving medical fluids such as continuous positive airway pressure (CPAP) machines. In some implementations, the machine may be configured for use in a patient's home (e.g., a home dialysis machine, home CPAP machine). The home machine may take the form of a peritoneal dialysis machine.

An exemplary method of protecting tubing connecting a patient to a treatment system, e.g., a peritoneal dialysis machine, in accordance with the present disclosure may include a tubing protector. A length of tubing, e.g., a portion of, or the entirety of, a line extending from the treatment system to a patient, may be received in a tubing sheath of the tubing protector. The portion may be closest to the patient to accommodate the tubing, and any connection of the tubing to a catheter, at an insertion point into the abdomen of the patient. The tubing sheath may be configured to minimize collapse, kinking, or blockage, or combinations thereof, along the length of the tubing received within the sheath. The tubing may be connected to the patient, e.g., via a catheter extending out of the patient's abdomen. The tubing may be connected between the treatment system (e.g., a peritoneal dialysis machine such as a PD cycler) and the patient for performing the treatment.

A belt may be attached to the patient. The belt may be coupled to the tubing sheath and may be attached to the patient by connecting around the patient (e.g., around the patient's abdomen) to secure the tubing sheath and the length of the tubing received in the tubing sheath. The tubing sheath may protect the tubing such that an uninterrupted or substantially uninterrupted fluid flow may be provided through the length of tubing in the sheath, between the treatment system and the patient, during the treatment. The tubing sheath may include a first portion comprising a resilient material. The resilient material may be of a material and formed within the sheath to accommodate movements of the patient, and consequential reorienting of the tubing, while reinforcing the sheath to protect and/or minimize against tubing deformation, such as blocking, kinking and/or collapse, or combinations thereof, along the length of the tubing. A second portion of the sheath may comprise a flexible material and enclose the first portion. In embodiments, the first portion may be a coil, a plurality of rings, a woven mesh, or a solid tube, or combinations thereof, such that the first portion is extendable along the tubing. The second portion may include a slot extending along the tubing sheath.

At least one of a fluid temperature, a fluid flow rate, a fluid pressure, a kink, collapse or blockage of the tubing, or patient parameters, or combinations thereof, may be detected during the treatment. Sensors may be disposed in the tubing sheath and/or belt for detection of desired parameters. In response to detecting a change in a desired parameter, a signal may indicate its status to the patient and/or medical professional. For example, a signal may notify, warn, alert, and/or alarm, via the tubing protector and/or the treatment system, which may indicate to the patient a need to adjust the tubing and/or other parameters for further evaluation.

It is understood that the methods described herein do not have to be executed in the order described, or in any particular order. Moreover, various activities described with respect to the methods identified herein can be executed in serial or parallel fashion.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A tubing protector, comprising a tubing sheath, the sheath including:
   a proximal end arranged and configured to contact an abdomen of a patient;
   a distal end opposite the proximal end; and
   a cavity extending from the distal end to the proximal end, the cavity arranged and configured to receive tubing extending from a peritoneal dialysis machine to the abdomen of the patient to perform dialysis, the cavity having a first diameter at the proximal end and a second diameter at the distal end, the second diameter being different than the first diameter; the sheath further comprising:
      a first portion for receiving and protecting a length of tubing extendable therein, so as to minimize collapsing, kinking, or blockage, or combinations thereof, along the length of the tubing;
      a second portion enclosing the first portion, the second portion comprising a flexible material; and
      wherein the first portion comprises a resilient material, the resilient material allowing for movement in the sheath and having a strength to allow for reorientation of the tubing, while withstanding deformation of the length of the tubing.

2. The tubing protector according to claim 1, further comprising a belt connected to the proximal end of the tubing sheath and removably attachable to a patient, the belt being arranged and configured to surround a waist of the patient.

3. The tubing protector according to claim 1, wherein the first portion is a coil, a plurality of rings, a woven mesh, or a solid tube, or combinations thereof, such that the first portion is extendable along the length of the tubing.

4. The tubing protector according to claim 1, wherein the second portion is a cover over the first portion and extendable along the length of the tubing.

5. The tubing protector according to claim 4, wherein the second portion includes a slot extending along the cover and the length of the tubing.

6. The tubing protector according to claim 2, further comprising one or more sensors configured to detect a fluid temperature, a fluid flow rate, a fluid pressure, a kink, collapse or blockage of the tubing, or patient parameters, or combinations thereof.

7. The tubing protector according to claim 6, the tubing sheath, or the belt, or both, further comprising a connectivity component for data transmission between one or more sensors and the peritoneal dialysis machine.

8. A tubing protection system, comprising:
   a tubing sheath including:
      a proximal end arranged and configured to contact an abdomen of a patient;
      a distal end opposite the proximal end; and
      a cavity extending from the distal end to the proximal end, the cavity arranged and configured to surround a length of tubing extendable from a peritoneal dialysis machine to the abdomen of the patient to perform dialysis, the cavity having a first diameter at the proximal end and a second diameter at the distal end, the second diameter being different than the first diameter, the tubing sheath arranged and configured to minimize collapsing, kinking, or blockage, or combinations thereof, along the length of the tubing;
   wherein the tubing sheath comprises a resilient material, the resilient material allowing for movement in the sheath, and having a strength to allow for reorientation of the tubing, while withstanding deformation of the length of the tubing.

9. The tubing protection system according to claim 8, wherein the tubing sheath includes a coil, a plurality of rings, a woven mesh, or a solid tube, or combinations thereof.

10. The tubing protection system according to claim 8, wherein the tubing sheath includes a cover.

11. The tubing protection system according to claim 8, further comprising a belt coupled to a proximal end of the tubing sheath, wherein the belt is removably attachable to the patient such that the tubing sheath is positionable about the length of the tubing when attached to the patient.

12. The tubing protection system according to claim 11, further comprising:
one or more sensors disposed on the tubing sheath, the cover, or the belt, or combinations thereof;
wherein the sensors are configured to detect a fluid temperature, a fluid flow rate, a fluid pressure, a kink, collapse or blockage of the tubing, or patient parameters, or combinations thereof.

13. The tubing protection system according to claim 10, wherein the cover includes a slot extending along the length of the tubing.

14. The tubing protection system according to claim 12, further comprising a connectivity component for data transmission to a remote device.

15. A method of protecting tubing connecting a patient to a peritoneal dialysis machine during a treatment, comprising:
receiving a length of the tubing closest to the patient in a tubing sheath, the sheath including: a proximal end arranged and configured to contact an abdomen of a patient, a distal end opposite the proximal end, and a cavity extending from the distal end to the proximal end, the cavity arranged and configured to surround the length of tubing, the cavity having a first diameter at the proximal end and a second diameter at the distal end, the second diameter being different than the first diameter, the sheath configured to minimize collapsing, kinking, or blockage, or combinations thereof, along the length of the tubing;
connecting the tubing to the patient for performing the treatment with the peritoneal dialysis machine; and
attaching a belt around the patient to secure the tubing sheath and the length of the tubing received in the tubing sheath, the belt being coupled to the tubing sheath, such that a substantially uninterrupted fluid flow is provided through the length of the tubing between the peritoneal dialysis machine and the patient during the treatment.

16. The method according to claim 15, further comprising detecting at least one of fluid temperature, a fluid flow rate, a fluid pressure, a kink, collapse or blockage of the tubing, or patient parameters, or combinations thereof, during the treatment.

17. The method according to claim 15, wherein the tubing sheath includes a first portion comprising a resilient material and having a strength to prevent deformation of the length of the tubing, and a second portion formed of a flexible material and enclosing the first portion.

18. The method according to claim 17, wherein the first portion is a coil, a plurality of rings, a woven mesh, or a solid tube, or combinations thereof, such that the first portion is extendable along the length of the tubing.

19. The method according to claim 17, wherein the second portion comprises a cover that includes a slot extending along the length of the tubing.

* * * * *

UNITED STATES PATENT AND TRADEMARK OFFICE
CERTIFICATE OF CORRECTION

| | |
|---|---|
| PATENT NO. | : 11,179,508 B2 |
| APPLICATION NO. | : 16/391576 |
| DATED | : November 23, 2021 |
| INVENTOR(S) | : David Yuds et al. |

It is certified that error appears in the above-identified patent and that said Letters Patent is hereby corrected as shown below:

On the Title Page

Item (72) -- Remove "Eric J. Bergman, Kalispell, MT" and insert -- Eric Bergman, Newton, MA --

Signed and Sealed this
Seventh Day of February, 2023

Katherine Kelly Vidal
*Director of the United States Patent and Trademark Office*